United States Patent [19]
Elliott et al.

[11] Patent Number: 5,143,719
[45] Date of Patent: Sep. 1, 1992

[54] ANTICALCULUS ORAL COMPOSITION CONTAINING COMBINATIONS OF ORGANOPHOSPHORUS POLYCARBOXYLATE COTELOMERS AND INORGANIC POLYPHOSPHATE SALTS

[75] Inventors: David L. Elliott, Hawthorne; Catherine L. Howie-Meyers, Bloomingdale, both of N.J.

[73] Assignee: Chesebrough-Pond's USA Co., Greenwich, Conn.

[21] Appl. No.: 686,208

[22] Filed: Apr. 16, 1991

[51] Int. Cl.$^5$ .................................................. A61K 7/16
[52] U.S. Cl. ........................................ 424/52; 424/49; 424/57
[58] Field of Search ................................. 424/49–58

[56] References Cited

U.S. PATENT DOCUMENTS

| | | | |
|---|---|---|---|
| Re. 29,182 | 4/1977 | McCune et al. | 424/49 |
| 3,429,963 | 2/1969 | Shedlovsky | 424/56 |
| 3,671,644 | 6/1972 | Irani et al. | 514/731 |
| 3,678,154 | 7/1972 | Widder et al. | 424/52 |
| 3,934,002 | 1/1976 | Haefele | 424/56 |
| 4,025,616 | 5/1977 | Haefele | 424/52 |
| 4,110,083 | 8/1978 | Benedict | 424/49 |
| 4,123,512 | 10/1978 | Gaffar | 424/52 |
| 4,157,387 | 6/1979 | Benedict | 424/49 |
| 4,183,914 | 1/1980 | Gaffar et al. | 424/48 |
| 4,207,405 | 6/1980 | Masler, III et al. | |
| 4,446,028 | 5/1984 | Becker | |
| 4,515,772 | 5/1985 | Parran, Jr. et al. | 424/57 |
| 4,534,866 | 8/1985 | Becker | |
| 4,590,066 | 5/1986 | Parran, Jr. et al. | 424/52 |
| 4,627,977 | 12/1986 | Gaffar et al. | 424/52 |
| 4,661,341 | 4/1987 | Benedict et al. | 424/48 |
| 4,663,202 | 5/1987 | Causton | |
| 4,681,686 | 7/1987 | Richardson et al. | |
| 4,684,518 | 8/1987 | Parran, Jr. et al. | 424/52 |
| 4,732,617 | 3/1988 | Causton et al. | 424/52 |
| 4,806,340 | 2/1989 | Gaffar et al. | 424/52 |
| 4,806,342 | 2/1989 | Gaffar et al. | 424/52 |
| 4,808,400 | 2/1989 | Gaffar et al. | 424/52 |
| 4,842,847 | 6/1989 | Amjad | 424/52 |
| 4,847,070 | 7/1989 | Pyrz et al. | 424/52 |
| 4,877,603 | 10/1989 | Degenhardt et al. | |
| 4,892,724 | 1/1990 | Amjad | 424/52 |
| 4,892,725 | 1/1990 | Amjad | 424/52 |
| 5,011,682 | 4/1991 | Elliott et al. | 424/52 |

*Primary Examiner*—Shep K. Rose
*Attorney, Agent, or Firm*—Milton L. Honig

[57] ABSTRACT

A method and composition for controlling calculus formation in the mouth is reported based upon a combination of inorganic polyphosphates and certain low molecular weight copolymers. These copolymers are formed from a mixture of mono- and di-carboxylic vinyl monomers reacted with hypophosphite groups. Particularly effective are phosphorous containing acrylate/maleate polymers of weight averaged molecular weight ranging from about 400 to 5000.

13 Claims, No Drawings

ANTICALCULUS ORAL COMPOSITION CONTAINING COMBINATIONS OF ORGANOPHOSPHORUS POLYCARBOXYLATE COTELOMERS AND INORGANIC POLYPHOSPHATE SALTS

CROSS-REFERENCES

Related patents and applications are as follows: U.S. Pat. No. 5,011,682 having Ser. No. 510,651, issued Apr. 30, 1991; U.S. patent application Ser. No. 680,652, filed Apr. 4, 1991; and U.S. patent application Ser. No. 686,106, filed Apr. 16, 1991.

BACKGROUND OF THE INVENTION

1. Field of the Invention

The invention relates to new anticalculus agents, dentifrice compositions containing these agents and use of some compositions to control calculus accumulation on teeth.

2. The Related Art

Calculus is a hard, mineralized deposit which forms around teeth. This formation arises from deposition of crystals of calcium phosphate in the pellicle and the extracellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective anticalculus agents.

Soluble inorganic pyrophosphate salts have over the last few years set the commercial standard as calculus or tartar control agents. This technology has been reported by Parran, Jr. et al. in a series of patents including U.S. Pat. Nos. 4,590,066, 4,515,772 and 4,684,518.

Anionic polymers, especially carboxylate group functionalized polymers, have been widely reported as effective against calculus Typically, low molecular weight anionic materials of high charge density are preferred in most of the prior art. For example, U.S. Pat. No. 4,661,341 (Benedict et al.) discloses the use of low molecular weight polyacrylic acids (MW range 3500 to 7500) in dental composition U.S. Pat. No. 3,429,963 (Shedlovsky) teaches use of maleate-containing copolymers and vinyl sulfonates in toothpaste. U.S. Pat. No. 4,183,914 (Gaffar et al.) reports use of polymaleates as anticalculus agents. The materials of Gaffar et al. cannot be obtained above molecular weight 1,000 and often have low purity in available commercial samples. High levels of impurities result in polymeric materials of poor appearance, taste and inadequate safety.

Commercially most significant has been the use of synthetic, linear anionic polymers of higher molecular weight in combination with the inorganic pyrophosphates. This technology derives from work done by Gaffar et al. reported in a series of patents including U.S. Pat. Nos. 4,627,977, 4,806,340, 4,806,342, 4,808,400 and U.S. 4,808,401. Anionic polymers described therein were found to inhibit the action of pyrophosphatases in the mouth and thereby allow greater efficacy of the inorganic pyrophosphate. The commercially operative polymer is a methyl vinyl ether/maleic anhydride copolymer, available under the GAF trademark Gantrez.

Organic phosphonic acid derivatives, some in polyxeric form, have been disclosed in U.S. Pat. No. 3,934,002 (Haefele). U.S. Pat. No. 4,892,724 (Amjad) cites a tartar inhibiting oral composition that includes a fluoride source, a dental abrasive, a carboxylate polymer and various phosphonic acids and their derivatives. A phosphated acrylic acid/hydroxyethyl methacrylate-/alkyl methacrylic acid ester copolymer has been suggested in GB 2 139 635B (Causton) as useful in an oral composition for treating teeth. U.S. Pat. No. 4,892,725 (Amjad) reports a fluoride oral composition with an anticalculus agent that includes a first polymer selected from homopolymers of carboxyl monomers and a second polymer which is a copolymer containing at least 30% of the carboxyl monomer. Related to this disclosure is U.S. Pat. No. 4,842,847 (Amjad) focusing upon a fluoride containing oral composition having an anticalculus agent selected from homo and copolymers, the latter containing at least 30% by weight of monocarboxylic or dicarboxylic monomer units. Combinations of polyacrylic acid derivatives, strontium and fluoride ion sources along with a soluble pyrophosphate have been reported in U.S. Pat. No. 4,847,070 (Pyrz et al.).

Evident from the foregoing review of the art is the considerable effort expended to devise better calculus control compositions. By no means, however, has any of the reported art been able to more than attenuate the problem. There is considerable room for improvement over the known control agents.

Accordingly, it is an object of the present invention to provide a material of improved efficacy in controlling formation of calculus.

A still further object of the present invention is to provide a tartar control agent of improved taste, safety and appearance.

These and other objects of the present invention will become more apparent in light of the detailed description and examples which follow.

SUMMARY OF THE INVENTION

An oral composition is provided comprising:
(i) about 0.1 to about 10% of at least one inorganic polyphosphate salt;
(ii) a polymer present in are effective amount to control build-up of tartar, said polymer having the formula I:

wherein A is a random polymeric residue comprising at least one unit of structure II,

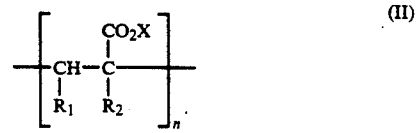

at least one unit of structure III, different from a unit of structure II,

(I)

wherein A is a random polymeric residue comprising at least one unit of structure II,

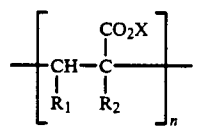

(II)

and at least one unit of structure III, different from a unit of structure II,

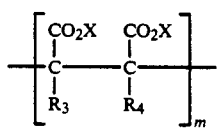

(III)

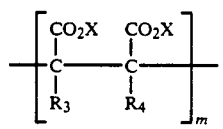

(III)

and B is hydrogen or a residue A; m and n are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

DETAILED DESCRIPTION

Now it has been found that combinations of inorganic polyphosphates such as pyrophosphate and phosphono-containing cotelomers of acrylic acid/maleic acid (or other carboxylic monomers) give beneficial activity in oral compositions as anticalculus agents. Combinations of these agents are found to have anticalculus activity which is greater than either material alone.

The inorganic polyphosphate salt may be a linear molecularly dehydrated polyphosphate and generally employed in the form of a wholly or partially neutralized water soluble alkaline metal or ammonium salt, and any mixtures thereof. Its representative examples include sodium hexametaphosphate, sodium tripolyphosphate, disodium diacidpyrophosphate, trisodium monoacid and tetrasodium pyrophosphates and similar potassium salts. Linear polyphosphates correspond to $(NaPO_3)_n$ where n is from about 2 to about 125. They are generally employed in the instant oral compositions in approximate weight from about 0.1 to about 10%, preferably from about 0.5 to about 6%, more preferably from about 2 to 5% by weight. When n is at least 3 in $(NaPO_3)n$, the polyphosphates are glassy in character.

The polymers of the present invention which are effective antitartar agents and which act in conjunction with the inorganic polyphosphates are copolymers of, for example, acrylic acid and maleic acid (and other carboxylic monomers) whose structure is modified to include mono- or di-substituted hypophosphite units along the polymer backbone. These materials are different in structure from typical acrylate/maleate copolymers in two respects. First, as noted they contain phosphite or hypophosphite groups. Secondly, they are of unusually low molecular weight. Materials with this structure are superior, as shown by in vitro and in vivo tests, to polyacrylates such as disclosed by Benedict et al. in U.S. Pat. No. 4,661,341 or polymaleates disclosed by Gaffar et al. in U.S. Pat. No. 4,183,914.

Based upon the herein disclosed studies, it is necessary that the polymers of this invention be comprised of three essential components. There must be present a monocarboxylic acid monomer, a dicarboxylic acid monomer, and a hypophosphite, which when reacted will form polymers of this invention. Absent any of these components, the resultant polymers will not be as effective.

The general structure of the polymers of this invention are as follows:

and B is hydrogen or a residue A; m and n are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

Polymers forming the structure II will have a single carboxylic acid or salt group. There will be anywhere from 3 to 7 carbon atoms for this structure. Suitable monomers include acrylic acid, methacrylic acid, alpha-substituted alkyl acrylic acids, and beta-carboxyalkyl acrylates.

Monomers that form structure III will have at least two carboxylic acid groups and may range from 4 to 7 carbon atoms in size. Suitable monomers include maleic acid, fumaric acid, itaconic acid, mesaconic acid, citraconic acid, their anhydrides or salts.

Specific salts of the mono- and di- carboxylic monomers may be those including the counterions of sodium, potassium, calcium, strontium, zinc, copper, ammonium, $C_2$—$C_9$ alkanolammonium, $C_1$—$C_8$ alkyl amine and mixtures thereof. Strontium and zinc are particularly preferred counterions.

Most preferred are copolymers formed from acrylic acid and maleic acid.

Polymers of this invention are telomeric. Sodium hypophosphite is present in the polymerization medium to control molecular weight and to be incorporated into the backbone as mono- or di-substituted hypophosphite groups. These groups may be incorporated at the chain end or between monomer units in the chain. Typically, 70–90% of the total hypophosphite groups will be di-substituted. These groups are essential for the enhanced benefit of the polymers of this invention.

Molar ratio of total monomer to hypophosphite of the raw components before polymerization may range from about 40:1 to about 1:1, preferably from about 20:1 to about 4:1, optimally between about 16:1 to about 7:1. Lower ratios of monomer to hypophosphite generally result in lower polymer molecular weight and higher levels of incorporation of hypophosphite in the polymers.

Dicarboxylic monomers should be present in amounts in the copolymer ranging from about 10 to about 95 mole percent, preferably from about 20 to about 75 mole percent. Molar ratios of monocarboxylic monomer to dicarboxylic monomer should preferably be from about 5:1 to about 1:5, optimally between about 4:1 to about 1:1.

Polymers of this invention should have a molecular weight in the range between about 400 to about 5000, with a range of about 600 to about 2500 being preferred. These polymers will be present in the oral compositions in amounts ranging from about 0.01 to about 10% by weight, preferably about 0.4 to about 7%, optimally between about 1 to about 5%.

The ratios of inorganic polyphosphate to cotelomer may range from about 1:10 to 10:1, preferably from about 4:1 to 1:4 by weight. The total of both materials in the oral compositions should range from about 0.1 to 10 weight percent, with 0.7 to 6.5% more preferred. Especially preferred is a combination of phosphonate cotelomer of acrylic acid and maleic acid having molecular weight between 600 and 2500 and acrylate/maleate ratio of about 1.5:1 and pyrophosphate or mixture of its salts.

Carriers suitable for use with the composition are preferably hydroxylic materials such as water, polyols and mixtures thereof. Polyols, sometimes referred to as humectants, include glycerol, sorbitol, propylene glycol, lactitol, xylitol, polypropylene glycol, polyethylene glycol, hydrogenated corn syrup and mixtures thereof. Particularly preferred as the carrier is a liquid mixture of 3-30% water, 0-80% glycerol and 20-80% sorbitol. Generally the amount of carrier will range from about 25 to 99.9% by weight, preferably from about 70 to 95% by weight.

When the compositions of this invention are in the form of a toothpaste or gel there will typically be included a natural or synthetic thickening agent in an amount from 0.1-10%, preferably about 0.5-5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans. The amount of thickening agent will generally be between about 0.1 and 10% by weight.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive Abrasives may be selected from water-insoluble alkali or alkaline earth metal salts of metaphosphate, calcium carbonate, aluminates and silicates. Especially preferred are silicate, dicalcium phosphate and calcium carbonate. Amounts of the abrasive will range from about 5% to about 80% by weight.

For anti-caries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.5 to 1% by weight.

Flavors that are usually present in the oral compositions are those based on oils of spearmint and peppermint. Examples of other flavoring materials include menthol, clove, wintergreen, eucalyptus and aniseed. Flavors may range in concentration from 0.1 to 5% by weight.

Sweetening agents such as saccharin, sodium cyclamate, aspartame, sucrose and the like may be included at levels from about 0.1 to about 5% by weight.

Other additives may also be incorporated into the oral compositions including preservatives, silicones, other synthetic or natural polymers and anti-gingivitis actives.

The following examples will more fully illustrate the embodiments of this invention. All parts, percentages and proportions referred to herein and in the appended claims are by weight of the total composition unless otherwise stated.

EXAMPLE 1

Table I summarizes key structural details of the polymer component of this invention.

TABLE I

| Sample | Acrylate/Maleate Ratio | Monomer/ Hypophosphite Ratio | Molecular Wt. | |
|---|---|---|---|---|
| | | | Mw | Mn |
| AM-C | 1.5:1 | 8:1 | 1200 | 700 |
| AM-D | 1.5:1 | 16:1 | 2100 | 1000 |
| AM-H | 2:1 | 32:1 | 4400 | 1700 |

These polymers were prepared from acrylic acid and maleic acid using sodium hypophosphite to promote telomerization. In a typical reaction, sodium hypophosphite monohydrate of a desired amount was added to deionized water and the solution heated to about 90°-100° C. Maleic anhydride was added to the solution and pH adjusted to about 4. Sodium or potassium persulfate (1-10% of total monomer feed) was used to initiate the polymerization. Acrylic acid at the appropriate ratio was added periodically over a 2-4 hour time period. Polymerization was continued until substantially 100% conversion was obtained.

EXAMPLE 2 pH-STAT ASSAY

Combinations of inorganic polyphosphate and polymer of this invention were evaluated for calcium phosphate transformation inhibition activity using a pH-stat assay. The procedure for this assay was adapted from that of Gaffar et al. in U.S. Pat. No. 4,627,977. Table II gives the results from these tests using combinations of AM-C with soluble pyrophosphate. Combinations of pyrophosphate and Gantrez S-97 ®, a copolymer of maleic acid and methyl vinyl ether sold by GAF Corporation, are included for comparative purposes.

TABLE II

| Agent 1 (Conc.) | Agent 2 (Conc.) | Delay Time (min) | | |
|---|---|---|---|---|
| | | Actual | Expected | Difference |
| Pyro (3 ppm) | — | 4.8 | — | — |
| Pyro (5 ppm) | — | 11.0 | — | — |
| — | AM-C (5 ppm) | 2.2 | — | — |
| — | AM-C (10 ppm) | 4.3 | — | — |

TABLE II-continued

| Agent 1 (Conc.) | Agent 2 (Conc.) | Actual | Delay Time (min) Expected | Difference |
|---|---|---|---|---|
| — | AM-C (20 ppm) | 12.3 | — | — |
| Pyro (3 ppm) | AM-C (5 ppm) | 10.3 | 7.0 | +3.3 |
| Pyro (3 ppm) | AM-C (10 ppm) | 13.4 | 9.1 | +4.3 |
| Pyro (3 ppm) | AM-C (20 ppm) | 20.3 | 17.1 | +3.2 |
| Pyro (5 ppm) | AM-C (5 ppm) | 18.4 | 13.2 | +5.2 |
| Pyro (5 ppm) | AM-C (10 ppm) | 26.6 | 15.3 | +11.3 |
| Pyro (5 ppm) | AM-C (20 ppm) | 41.1 | 23.3 | +17.8 |
| Pyro (5 ppm) | Gantrez S-97 (3 ppm) | 10.7 | 11.0 | −0.3 |
| Pyro (5 ppm) | Gantrez S-97 (5 ppm) | 9.2 | 9.7 | −0.5 |
| Pyro (5 ppm) | Gantrez S-97 (30 ppm) | 7.1 | 9.7 | −2.6 |

More than additive behavior was observed for AM-C/pyrophosphate combinations, but not for Gantrez S-97/pyrophosphate combinations. The synergistic effect was more evident at the higher pyro concentration (5 ppm).

EXAMPLE 3

Brushite Seeded Growth Assay

This in vitro assay was designed to assess the ability of an agent to inhibit the growth of brushite crystals. To conduct the test, the desired amount of sample was placed in a centrifuge tube. Four mls of an imidazole buffer (pH 6.1) containing 10 mg of unstabilized brushite powder was placed in the tube. The sample was mixed for about 5 seconds with a vortex mixer. To the slurry was added 0.5 ml of a 53 mM calcium chloride solution and 0.5 ml of a 53 mM potassium phosphate dihydrate solution, and the slurry was mixed for about 5 seconds with a vortex mixer. The slurry was incubated at 37° C. on a rotary mixer for 1 hour. The sample was centrifuged and 30 μls of the supernatant was removed and analyzed for phosphorus content using the method of Chen et al. (*Anal. Chem.* 8, 1756 (1956)). A brushite sample (no agent) was typically run as a negative control. The buffer/brushite calcium chloride/potassium phosphate dihydrate solution was analyzed for phosphorus as a positive control. Values of % inhibition were calculated using the following relationship:

$$\% \text{ Inhibition} = \frac{\text{Sample } (mM \text{ Phosphorus}) - \text{Neg. Control } (mM \text{ Phosphorus})}{\text{Pos. Control } (mM \text{ Phosphorus}) - \text{Neg. Control } (mM \text{ Phosphorus})} \times 100$$

Table IV gives representative values of % Inhibition for the individual components of this invention which are measured and calculated as shown above.

TABLE III

Combinations of Polymer and Pyrophosphate in Brushite Seeded Growth

| Agent 1 (Conc.) | Agent 2 (Conc.) | % Inhibition 0.5 ppm | 1 ppm | 3 ppm | 4 ppm |
|---|---|---|---|---|---|
| Pyrophosphate | — | 4 | 6 | 35 | 92 |
| AM-C | — | 14 | 68 | 95 | 95 |

As shown in Table III, the polymer AM-C was more effective against brushite crystal growth inhibition than pyrophosphate. Combinations of the two agents are show in Table IV.

TABLE IV

Combinations of Pyrophosphate and Polymers in Seeded Brushite Growth Assay

| Agent 1 (Conc.) | Agent 2 (Conc.) | % Reduction Actual | Expected | Difference |
|---|---|---|---|---|
| Pyro (0.5 ppm) | AM-C (0.5 ppm) | 30% | 18% | +12% |
| Pyro (1 ppm) | AM-C (1 ppm) | 99% | 74% | +25% |

Combinations of the two agents display more than additive increases in activity over either of the agents alone. The expected values were calculated by adding the activities of the individual components from Table III.

EXAMPLE 4

The following formulation (shown in Table V) was prepared containing 5% AM-C and 1.3% pyrophosphate (mixture of potassium and sodium salts).

TABLE V

Toothpaste Formulation Containing AM-C and Pyrophosphate

| Ingredient | Weight |
|---|---|
| Sorbitol | 40–50 |
| Abrasive Silica | 8–10 |
| Thickening Silica | 8–12 |
| Thickener/Binder | 0.1–1.0 |
| Flavor | 0.5–0.8 |
| Sweetener | 0.3 |
| Sodium Lauryl Sulfate | 1–2 |
| Dye | ~0.001 |
| Alcohol | 1–2 |
| AM-C | 5.0 |
| Pyrophosphate | 1.3 |
| Sodium Fluoride | 0.2–0.3 |
| Water | q.s. to 100 |

Although this invention has been described with reference to specific examples, it will be apparent to one skilled in the art that various modifications may be made thereto which fall within its scope.

What is claimed is:

1. An oral dentifrice composition comprising:
   (i) about 0.1 to about 10% of at least one inorganic polyphosphate salt; and
   (ii) about 0.01 to about 10% of a polymer present to control build-up of tartar, said polymer having the formula I:

(I)

wherein A is a random polymeric residue comprising at least one unit of structure II,

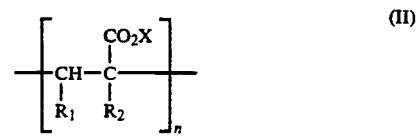

(II)

and at least one unit of structure III, different from a unit of structure II,

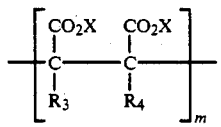

and B is a hydrogen or a residue A; m and n are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof, the molar ratio of structure II to structure III ranging from about 5:1 to about 1:5, structure II being formed from monomers selected from the group consisting of acrylic, methacrylic, alpha-substituted acrylic, betacarboxyalkyl acrylic acids or salts, and mixtures thereof, structure III being formed from monomers selected from the group consisting of maleic, fumaric, mesaconic, citraconic acid residues including their anhydrides or salts, and mixtures thereof, a molar ratio of total monomer to hypophosphite utilized to prepare the polymer ranging from about 40:1 to about 1:1, and wherein mono- or di-substituted hypophosphite groups are present at the chain end or between monomer units in the chain.

2. A composition according to claim 1 further comprising a dental abrasive present in an amount from about 5% to about 80% by weight.

3. A composition according to claim 1 further comprising an effective amount of a fluoride for prevention of caries.

4. A composition according to claim 1 wherein the molecular weight of the polymer ranges from about 600 to about 2500.

5. A composition according to claim 1 wherein said molar ratio of structure II to III ranges from about 4:1 to about 1:10.

6. A composition according to claim 1 wherein the polymer is formed from a combination of acrylic acid or salt and maleic anhydride, its acid or salt and sodium hypophosphite.

7. A composition according to claim 1 wherein said inorganic polyphosphate is a salt selected from the group consisting of hexametaphosphate, tripolyphosphate, pyrophosphate, acid pyrophosphate and mixtures thereof.

8. A composition according to claim 7 wherein said inorganic polyphosphate salt is a soluble pyrophosphate.

9. A composition according to claim 8 wherein said soluble pyrophosphate is present in an amount from about 1.5% to about 5% by weight.

10. A composition according to claim 1 wherein said polymer is present in an amount from about 0.75% to about 5% by weight.

11. A composition according to claim 7 wherein the inorganic polyphosphate is a mixture of sodium and potassium pyrophosphate in a ratio ranging from 1:5 to 5:1.

12. A composition according to claim 1 wherein the inorganic polyphosphate is trisodium monoacid pyrophosphate.

13. A method of controlling dental calculus which comprises treating teeth with a composition according to claim 1.

* * * * *

UNITED STATES PATENT AND TRADEMARK OFFICE
CERTIFICATE OF CORRECTION

PATENT NO. : 5,143,719
DATED : September 1, 1992
INVENTOR(S) : Elliott et al.

It is certified that error appears in the above-indentified patent and that said Letters Patent is hereby corrected as shown below:

Cover page   Item [73] Assignee        "Chesebrough-Pond's USA Co.,"

should read -- Chesebrough-Pond's USA Co., Division of Conopco, Inc. --

Signed and Sealed this

Twenty-fourth Day of May, 1994

Attest:

BRUCE LEHMAN

*Attesting Officer*        Commissioner of Patents and Trademarks